US008032303B2

(12) United States Patent
Fujisawa et al.

(10) Patent No.: US 8,032,303 B2
(45) Date of Patent: Oct. 4, 2011

(54) METHODS AND APPARATUS TO DETERMINE A CONCENTRATION OF NITROGEN IN A DOWNHOLE FLUID

(75) Inventors: Go Fujisawa, Sagamihara (JP); Chee Kin Khong, Shenzhen (CN); Oliver C. Mullins, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 501 days.

(21) Appl. No.: 12/277,262

(22) Filed: Nov. 24, 2008

(65) Prior Publication Data

US 2009/0143992 A1 Jun. 4, 2009

Related U.S. Application Data

(60) Provisional application No. 60/991,202, filed on Nov. 29, 2007.

(51) Int. Cl.
*G01V 1/40* (2006.01)
(52) U.S. Cl. ........................................................ 702/13
(58) Field of Classification Search ................... 702/13, 702/23, 24, 182–185, 188
See application file for complete search history.

(56) References Cited

U.S. PATENT DOCUMENTS

| | | | |
|---|---|---|---|
| 5,939,717 A | 8/1999 | Mullins | |
| 6,995,360 B2* | 2/2006 | Jones et al. | 250/269.1 |
| 2006/0243047 A1 | 11/2006 | Terabayashi et al. | |
| 2007/0143023 A1 | 6/2007 | Betancourt et al. | |
| 2007/0171413 A1 | 7/2007 | Vannufferen et al. | |

FOREIGN PATENT DOCUMENTS

EP 1865147 12/2007

* cited by examiner

*Primary Examiner* — Edward Raymond
(74) *Attorney, Agent, or Firm* — Daryl Wright; Jody DeStefanis; Jeff Griffin (57) ABSTRACT

Methods and apparatus to determine a concentration of nitrogen in a downhole fluid are described. An example apparatus to determine a concentration of nitrogen in a downhole fluid includes a fluid measurement unit to measure a first fluid composition and a density of at least a hydrocarbon and carbon dioxide in a sample of the downhole fluid. Additionally, the example apparatus includes one or more sensors to measure at least a pressure and a temperature of the sample. Further, the example apparatus includes a processing unit to determine a first theoretical density based on at least the first fluid composition, the temperature, and the pressure the sample. Further still, the example apparatus includes an analyzer to determine a first difference between the density of at least the hydrocarbon and the carbon dioxide in the sample and the first theoretical density. The first difference is associated with a concentration of nitrogen in the sample.

22 Claims, 7 Drawing Sheets

|  | C1 (wt%) | C2-C5 (wt%) | C6+ (wt%) | CO$_2$ (wt%) | N$_2$ (wt%) |
|---|---|---|---|---|---|
| FIELD MEASUREMENTS | 64 | 0 | 0 | 0 | 36 |
| LABORATORY ANALYSIS | 63.5 | 1.1 | 0 | 0.2 | 35.7 |

METHODS AND APPARATUS TO DETERMINE A CONCENTRATION OF NITROGEN IN A DOWNHOLE FLUID

RELATED APPLICATION

This patent claims priority to U.S. Provisional Patent Application No. 60/991,202, filed on Nov. 29, 2007, which is hereby incorporated herein by reference in its entirety.

FIELD OF THE DISCLOSURE

This patent relates generally to sampling and analyzing formation fluids and, more particularly, to methods and apparatus to determine a concentration of nitrogen in a downhole fluid.

BACKGROUND

Downhole fluid analysis is often used to provide information in real time about the composition of subterranean formation or reservoir fluids. Such real-time information can be advantageously used to improve or optimize the effectiveness of formation testing tools during sampling processes in a given well (e.g., downhole fluid composition analysis allows for reducing and/or optimizing the number of samples captured and brought back to the surface for further analysis). More generally, collecting accurate data about the characteristics of formation fluid(s) is an important aspect of making reliable predictions about a formation or reservoir and, thus, can have a significant impact on reservoir performance (e.g., production, quality, volume, efficiency, etc.).

To increase production of certain reservoirs such as, for example, the Cantarell field in Mexico, nonhydrocarbon fluids such as nitrogen are injected into the formation or into adjacent wellbores. However, in some cases, such injected nitrogen may bypass the formation fluid and/or not obtain an equilibrium state in the formation fluid, thereby reducing the benefits gained by injecting nitrogen into the formation. While there are many benefits of injecting nitrogen into a formation, nitrogen is not detectable using known downhole fluid analysis techniques. Therefore, in an attempt to determine the nitrogen concentration within a formation, numerous samples are typically obtained from the formation and brought back to the surface for analysis. However, these known techniques do not provide real-time information, which delays the ability to make production and/or sampling decisions based on the results of the analysis.

SUMMARY

An example apparatus to determine a concentration of nitrogen in a downhole fluid includes a fluid measurement unit to measure a first fluid composition and a density of at least a hydrocarbon and carbon dioxide in a sample of the downhole fluid. Additionally, the example apparatus includes one or more sensors to measure at least a pressure and a temperature of the sample. Further, the example apparatus includes a processing unit to determine a first theoretical density based on at least the first fluid composition, the temperature, and the pressure of the sample. Further still, the example apparatus includes an analyzer to determine a first difference between the density of at least the hydrocarbon and the carbon dioxide in the sample and the first theoretical density. The first difference is associated with a concentration of nitrogen in the sample.

An example method of determining a concentration of nitrogen in a downhole fluid includes obtaining a sample of a downhole fluid. Additionally, the example method includes analyzing the sample to determine a first fluid composition and a density of at least a hydrocarbon and carbon dioxide in the sample. Further, the example method includes measuring a pressure and a temperature of the sample. Further still, the example method includes determining a first theoretical density based on at least the first fluid composition, the temperature, and the pressure of the sample. Further yet, the example method includes determining a first difference between the density of at least the hydrocarbon and the carbon dioxide in the sample and the first theoretical density. The first difference is associated with the concentration of nitrogen in the sample.

DETAILED DESCRIPTION

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

The example methods and apparatus described herein can be used to determine the concentration of nitrogen in a downhole fluid. In particular, the example methods and apparatus described herein involve obtaining a fluid sample and increasing the pressure of the sample prior to analyzing the fluid sample. Additionally, the example methods and apparatus described herein involve measuring characteristics of the fluid sample and comparing these characteristics to known reference characteristics stored in a database to determine a theoretical density of the sample. Further, the example methods and apparatus described herein involve determining a difference, which is associated with a concentration of nitrogen in the sample, between a theoretical density and a measured density of the sample.

In one described example, a predetermined amount of fluid enters a flowline and the pressure of the fluid is increased. Once the pressure of the sample is the same as or within an acceptable deviation from a predetermined pressure, a fluid measurement unit measures the density and the composition of at least the hydrocarbon constituents and the carbon dioxide in the sample. Additionally, one or more sensors measure the pressure and the temperature of the sample. These measured characteristics are then compared to known reference characteristics to iteratively determine a theoretical fluid density and to iteratively adjust the fluid composition based on the determined nitrogen concentration in the sample until, for example, a difference between the theoretical fluid density and the measured fluid density, which includes the determined nitrogen concentration, is at or below a predetermined threshold or parameter or until a predetermined number of iterations have taken place.

Figure 1:
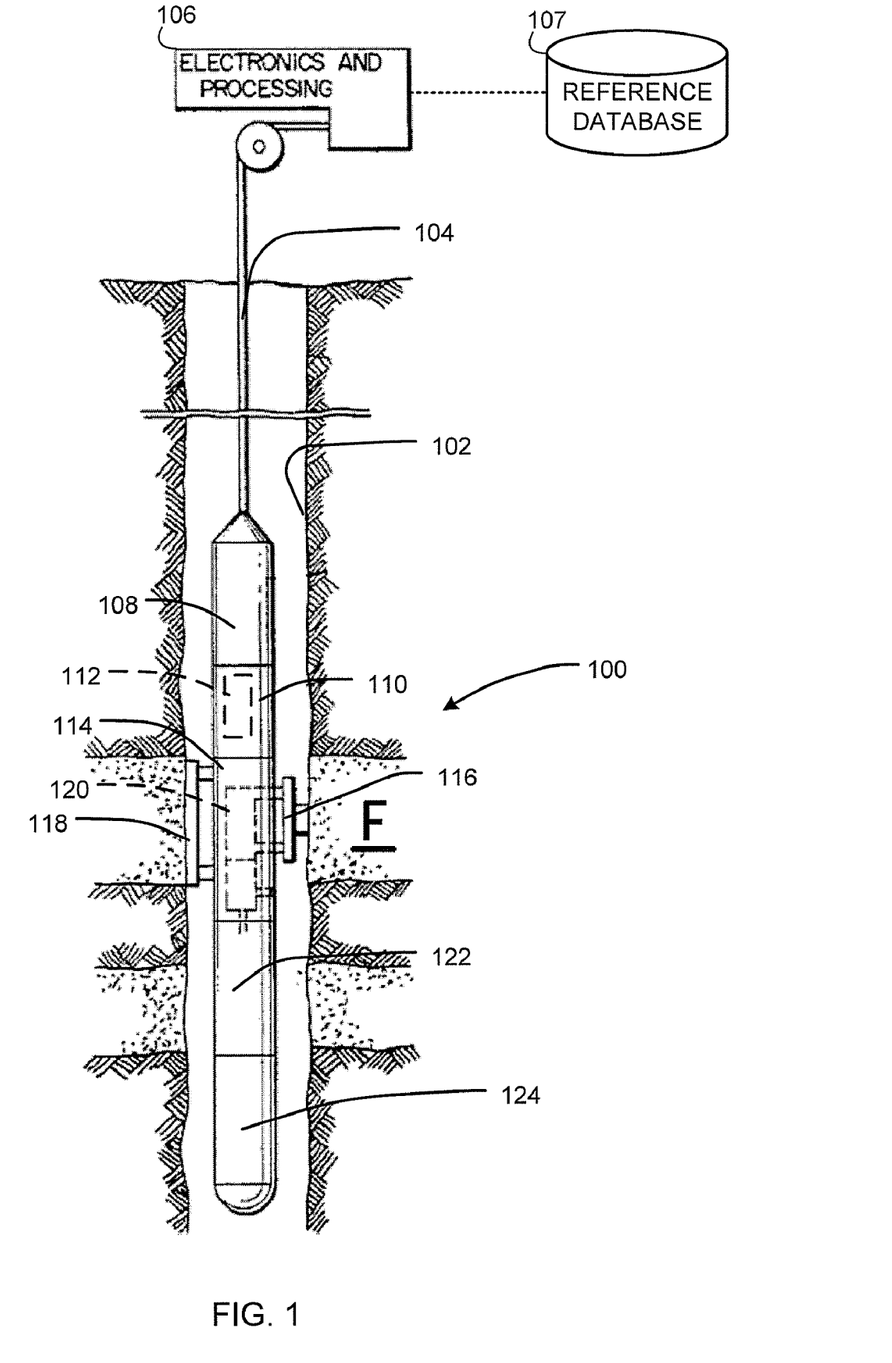
FIG. 1 depicts an example wireline tool that may be used to implement the methods and apparatus described herein.

FIG. 1 depicts an example wireline tool 100 that may be used to extract and analyze formation fluid samples and which may be used to determine a concentration of injected nitrogen, which is a substantially non-optically detectable fluid, within a formation fluid sample using the example methods and apparatus described herein. While the examples described herein refer to methods and apparatus to determine a concentration of injected nitrogen within a formation, the methods and apparatus described herein can be advantageously utilized to determine a concentration of naturally occurring non-optically detectable fluid such as, for example, nitrogen, hydrogen sulfide, and/or helium. While hydrogen sulfide has absorption in the near-infrared region, commercially available downhole fluid analysis tools such as, for example, the Composition Fluid Analyzer (CFA) and the InSitu Fluid Analyzer (IFA) tools provided by Schlumberger®, do not target the absorption peaks of hydrogen sulfide. Therefore, hydrogen sulfide is effectively considered a non-optically detectable fluid. As shown in FIG. 1, the example wireline tool 100 is suspended in a borehole or wellbore 102 from the lower end of a multiconductor cable 104 that is spooled on a winch (not shown) at the surface. At the surface, the cable 104 is communicatively coupled to an electronics and processing system 106. The electronics and processing system 106 may include or be communicatively coupled to a reference database 107 that may be used to store reference measurement values of reference formation fluids known to have particular fluid compositions, densities, and any other parameters or characteristics. The wireline tool 100 includes an elongated body 108 that includes a collar 110 having a downhole control system 112 configured to control extraction of formation fluid from a formation F, perform measurements on the extracted fluid, and to control the apparatus described herein to determine the concentration of nitrogen within a formation fluid sample.

The example wireline tool 100 also includes a formation tester 114 having a selectively extendable fluid admitting assembly 116 and a selectively extendable tool anchoring member 118 that are respectively arranged on opposite sides of the elongated body 108. The fluid admitting assembly 116 is configured to selectively seal off or isolate selected portions of the wall of the wellbore 102 to fluidly couple to the adjacent formation F and draw fluid samples from the formation F. The formation tester 114 also includes a fluid analysis module 120 through which the obtained fluid samples flow. The sample fluid may thereafter be expelled through a port (not shown) or it may be sent to one or more fluid collecting chambers 122 and 124, which may receive and retain the formation fluid samples for subsequent testing at the surface or a testing facility.

In the illustrated example, the electronics and processing system 106 and/or the downhole control system 112 are configured to control the fluid admitting assembly 116 to draw fluid samples from the formation F and to control the fluid analysis module 120 to measure the fluid samples. In some example implementations, the fluid analysis module 120 may be configured to analyze the measurement data of the fluid samples as described herein. In other example implementations, the fluid analysis module 120 may be configured to generate and store the measurement data and subsequently communicate the measurement data to the surface for analysis at the surface. Although the downhole control system 112 is shown as being implemented separate from the formation tester 114, in some example implementations, the downhole control system 112 may be implemented in the formation tester 114.

As described in greater detail below, the example wireline tool 100 may be used in conjunction with the example methods and apparatus described herein to determine the concentration of injected nitrogen and/or any naturally, occurring substantially non-optically detectable fluid in a formation fluid sample. For example, the formation tester 114 may include one or more sensors, fluid analyzers and/or fluid measurement units disposed adjacent a flowline and may be controlled by one or both of the downhole control system 112 and the electronics and processing system 106 to determine the composition of or a characteristic of fluid samples extracted from, for example, the formation F.

While the example methods and apparatus to determine a concentration of nitrogen within a formation fluid sample are described in connection with a wireline tool such as that shown in FIG. 1, the example methods and apparatus can be implemented with any other type of wellbore conveyance. For example, the example methods and apparatus can be implemented with a drill string including logging-while-drilling (LWD) and/or measurement-while-drilling (MWD) modules, coiled tubing, etc.

Figure 2:
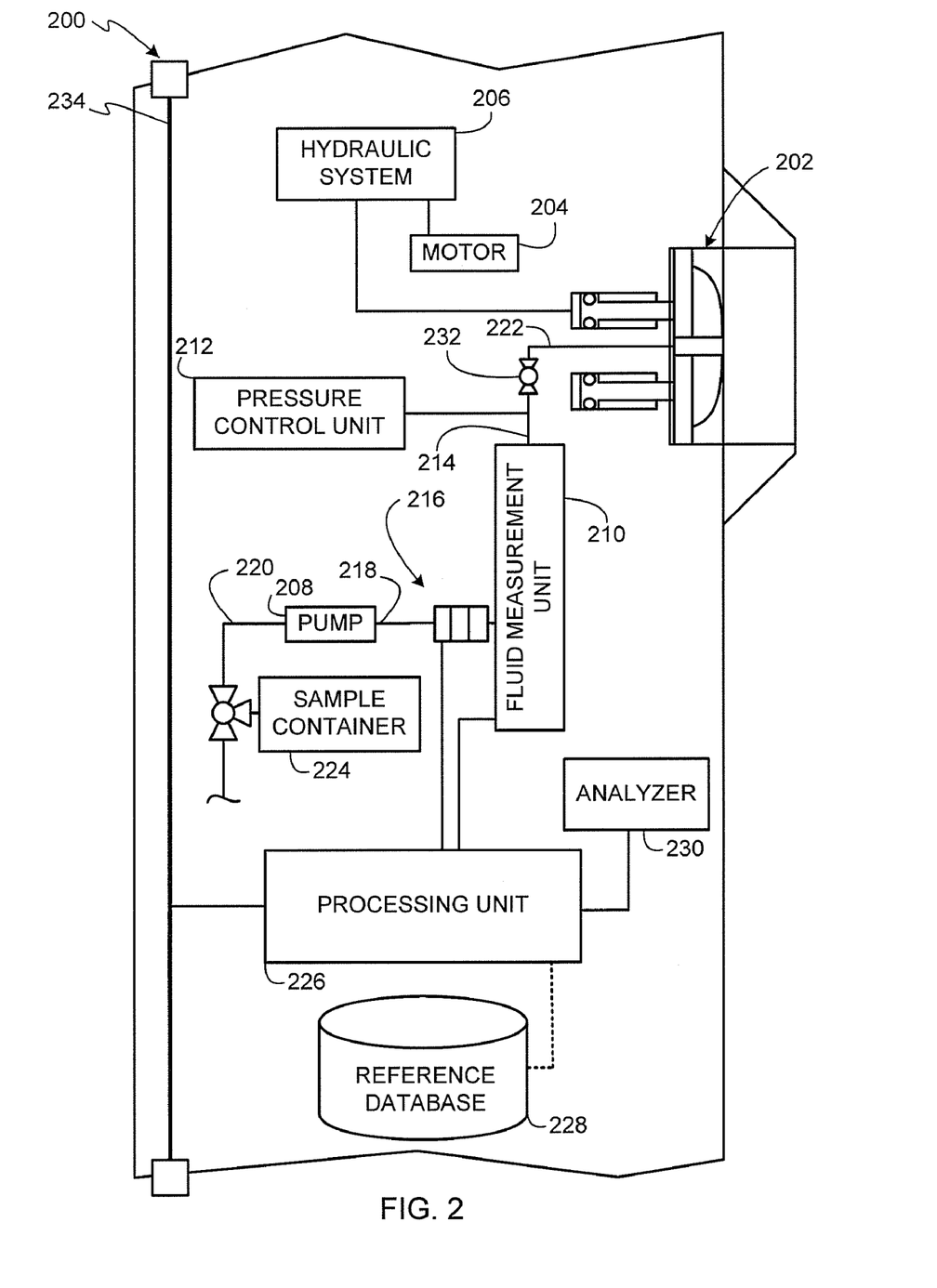
FIG. 2 is a simplified schematic illustration of an example manner in which the formation tester of FIG. 1 may be implemented.

FIG. 2 is a simplified schematic illustration of an example formation sampling tool 200 that may be used to implement the formation tester 114 of FIG. 1. The example formation sampling tool 200 includes a probe assembly 202 that can be selectively fluidly coupled to a surface of a wellbore via a motor 204 and a hydraulic system 206 to draw fluids from a formation (e.g., the formation F). In other example implementations, straddle packers (not shown) can additionally or alternatively be used to engage and isolate a portion of the surface of a wellbore to draw fluids from the formation. The formation sampling tool 200 is also provided with a pump 208 that may be used to draw fluids from the formation into the formation sampling tool 200.

The formation sampling tool 200 includes one or more fluid sensors to measure characteristics of the fluids drawn into the formation sampling tool 200. More specifically, in the illustrated example, the formation sampling tool 200 is provided with a fluid measurement unit 210 to measure one or more characteristics of formation fluids. The formation fluids may comprise at least one of a heavy oil, a bitumen, a volatile oil, a gas condensate, a wet gas, a dry gas, a drilling fluid, a wellbore fluid or, more generally, any fluid extracted from a subsurface formation. The fluid measurement unit 210 may be implemented using, for example, a light absorption spectrometer having a plurality of channels, each of which may correspond to a different wavelength. Thus, the fluid measurement unit 210 may be used to measure spectral information for fluids drawn from a formation. In other implementations, the fluid measurement unit 210 may be implemented using a VIS/NIR spectrometer, a VIS spectrometer, an NIR spectrometer or any other suitable spectrometer. Some commercially available fluid measurement units 210 include the Composition Fluid Analyzer (CFA) and InSitu Fluid Analyzer (IFA) provided by Schlumberger®.

In practice, if a VIS/NIR spectrometer is used to implement the formation sampling tool 200, the pressure of the sample may be increased by a pressure control unit 212 that changes (e.g., increases) the pressure of the fluid sample within a flowline 214 to increase the density of the sample. Specifically, increasing the density of the sample may increase the accuracy of some measurements obtained by the fluid measurement unit 210 such as, for example, when the sample is a highly compressive gas at a relatively low pressure. However, in other example implementations, the formation sampling tool 200 may not be provided with the pressure control unit 212.

The fluid measurement unit 210 is to obtain measurements from the sample having the increased pressure to determine, for example, a fluid composition of hydrocarbon(s) and carbon dioxide, which are substantially optically detectable fluids, in the fluid sample. Additionally, the fluid measurement unit 210 determines a density (e.g., a partial density) and/or a concentration of hydrocarbon constituents and carbon dioxide within the fluid sample. Each of the above described implementations of the fluid measurement unit 210 may be used to measure spectral information for fluids drawn from a formation and/or to measure any other characteristic(s) of the fluids. Such spectral information may include characteristic values such as optical density values associated with each of the channels and may be used to, for example, determine the composition of the fluid(s).

The formation sampling tool 200 is also provided with one or more sensors 216 to measure pressure, temperature, density, fluid resistivity, viscosity, and/or any other fluid properties or characteristics. While the sensors 216 are depicted as being in-line with a flowline 218, one or more of the sensors 216 may be used in other flowlines 214, 220, and 222 within the example formation sampling tool 200. In some examples, one or more of the sensors 216 may be a density sensor such as, for example, the InSitu Density densitometer provided by Schlumberger®. Alternatively, density may be determined using x-ray attenuation and/or gamma-ray attenuation. In other examples, a density value may be derived from a pressure gradient commonly practiced in oilfield analysis using a formation tester such as, for example, the Modular formation Dynamics Tester (MDT) provided by Schlumberger®. As depicted in Equations 1, 2, 3, 4 below, the weight percent of C1wt %, C2-C5wt %, C6+wt % and $CO_2$wt % may each be determined by dividing the density (e.g., the partial density) of each of C1, C2-C5, C6+ and $CO_2$wt % by the total density of the fluid (e.g., determined using the fluid measurement unit 210 as noted above).

$$\text{C1wt \%=C1 Partial Density/Total Density} \quad \text{Equation 1}$$

$$\text{C2-C15wt \%=C2-C5 Partial Density/Total Density} \quad \text{Equation 2}$$

$$\text{C6+wt \%=C6+Partial Density/Total Density} \quad \text{Equation 3}$$

$$CO_2\text{wt \%=}CO_2\text{ Partial Density/Total Density} \quad \text{Equation 4}$$

As depicted in Equations 5 and 6 below, the partial density (e.g., determined using the fluid measurement unit 210 as noted above) (e.g., 0.4 g/cc having 0.3 g/cc methane and 0.1 g/cc carbon dioxide) is subtracted from the measured fluid density (e.g., 0.5 g/cc) to determine a density difference (0.1 g/cc) that may be associated with a concentration of nitrogen in the sample. More specifically, as depicted in Equation 6, to determine the density of a substantially non-optically detectable fluid (e.g., nitrogen), the partial densities (e.g., C1, C2-C5, C6+ and $CO_2$) are subtracted from the of total density of the fluid (e.g., determined using the fluid measurement unit 210 as noted above).

$$\text{Nitrogen Concentration=Fluid Density−Partial Density} \quad \text{Equation 5}$$

$$\text{Density of Substantially Non-Optically Detectable Fluid=(Total Density)−(C1 Partial Density)−(C2-C5 Partial Density)−(C6+Partial Density)−(}CO_2\text{ Partial Density)} \quad \text{Equation 6}$$

As depicted in Equation 7 below, to determine the weight percent of the substantially non-optically detectable fluid, the weight percent of C1wt %, C2-C5wt %, C6+wt % and $CO_2$wt % are each subtracted from 100%.

$$\text{Weight Percent of Substantially Non-Optically Detectable Fluid=100\%−C1wt \%−C2-C5wt \%−C6+wt \%−}CO_2\text{wt \%} \quad \text{Equation 7}$$

The formation sampling tool 200 may also include a fluid sample container or store 224 including one or more fluid sample chambers in which formation fluid(s) recovered during sampling operations can be stored and brought to the surface for further analyses and/or confirmation of downhole analyses. In other example implementations, the fluid measurement unit 210 and/or the sensors 216 may be positioned in any other suitable position such as, for example, between the pump 208 and the fluid sample container or store 224.

To store, analyze and/or process test and measurement data (or any other data acquired by the formation sampling tool 200), the formation sampling tool 200 is provided with a processing unit 226 that may be communicatively coupled to a reference database 228, which may be used to store measurement values of reference formation fluids known to have particular fluid compositions and densities. Additionally, the processing unit 226 may be communicatively coupled to an analyzer 230 that at least determines a difference between one or more measured characteristic(s) of formation fluids and one or more theoretical characteristic(s) of the formation fluids.

Figure 7:
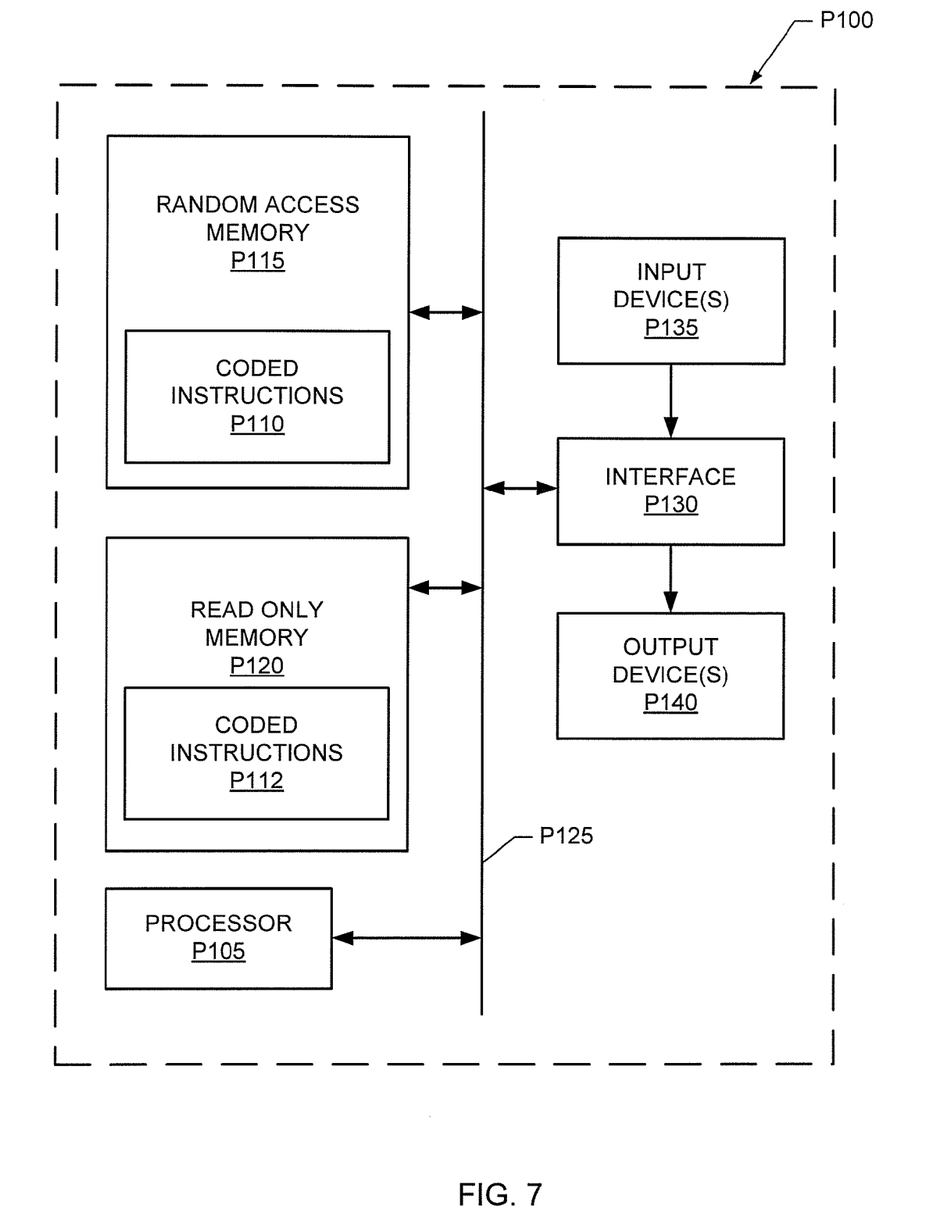
FIG. 7 is a schematic illustration of an example processor platform that may be used and/or programmed to implement any or all of the example methods and apparatus described herein.

The processing unit 226 may be generally implemented as shown in FIG. 7. In the illustrated example, the processing unit 226 may include a processor (e.g., a CPU and random access memory such as shown in FIG. 7) to control operations of the formation sampling tool 200 and implement measurement routines. For example, the processing unit 226 may be used to control the fluid measurement unit 210 to perform spectral measurements of fluid characteristics of formation fluid, to actuate a valve 232 to enable a fluid sample to flow into the flowline 214, and to determine a concentration of nitrogen within a formation fluid sample. Specifically, as described in more detail below, the processing unit 226 may be advantageously utilized to iteratively determine a theoretical density and/or to iteratively adjust a calculated or measured fluid composition of the sample based at least in part on the measured fluid composition of hydrocarbon constituents and carbon dioxide in the sample, the measured pressure and the temperature of the sample, as well as the determined concentration of nitrogen in the sample. The processing unit 226 may further include any combination of digital and/or analog circuitry needed to interface with the sensors 216 and/or the fluid measurement unit 210.

To store machine readable instructions (e.g., code, software, etc.) that, when executed by the processing unit 226, cause the processing unit 226 to implement measurement processes or any other processes described herein, the processing unit 226 may be provided with an electronic programmable read only memory (EPROM) or any other type of memory (not shown). To communicate information when the formation sampling tool 200 is downhole, the processing unit 226 is communicatively coupled to a tool bus 234, which may be communicatively coupled to a surface system (e.g., the electronics and processing system 106).

Although the components of FIG. 2 are shown and described above as being communicatively coupled and arranged in a particular configuration, the components of the formation sampling tool 200 can be communicatively coupled and/or arranged differently than depicted in FIG. 2 without departing from the scope of the present disclosure. In addition, the example methods and apparatus described herein are not limited to a particular conveyance type but, instead, may be implemented in connection with different conveyance types including, for example, coiled tubing, wireline, wired-drill-pipe, and/or other conveyance means known in the industry.

Figure 3:
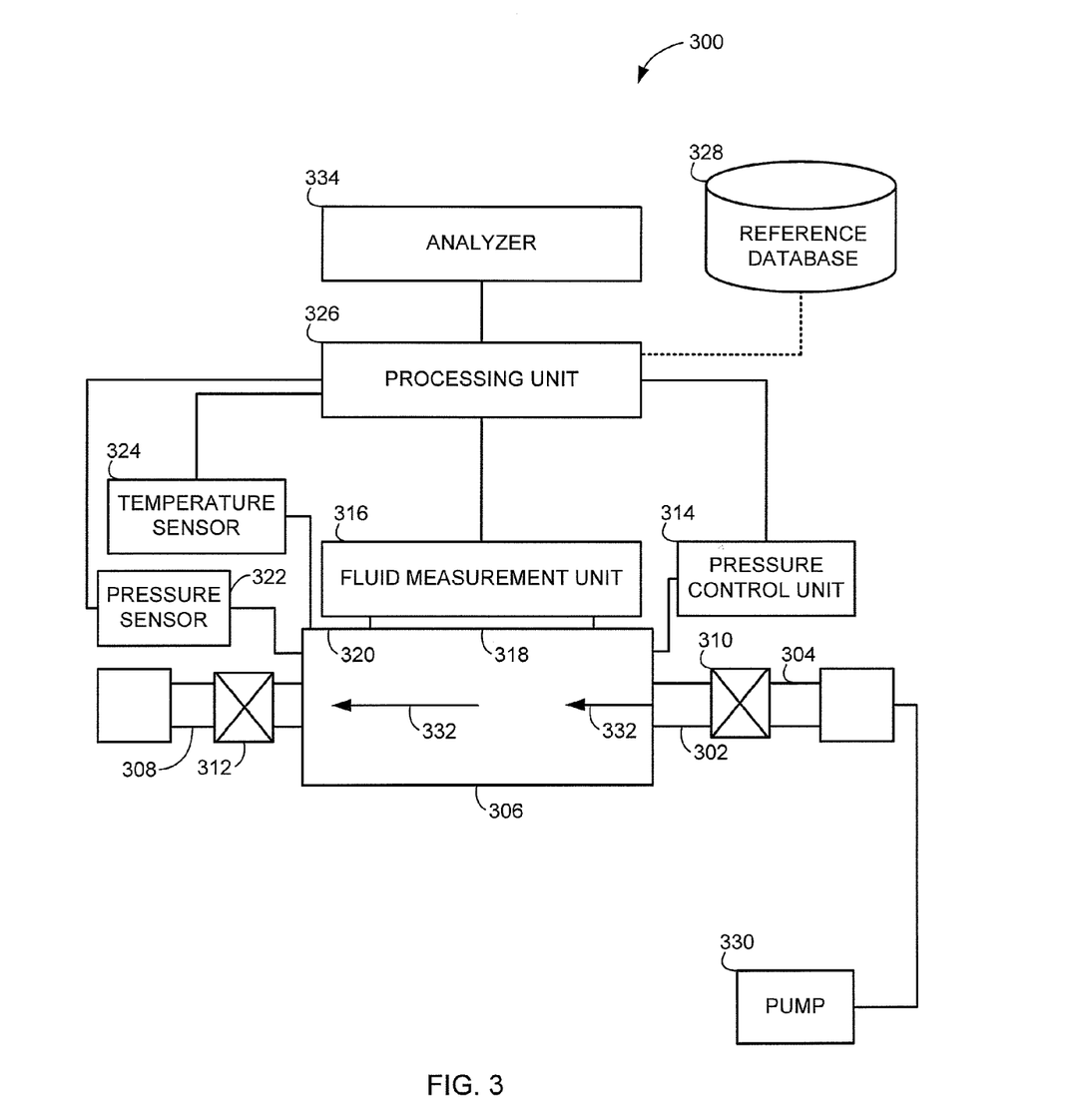
FIG. 3 is a schematic illustration of an example apparatus that may be used to implement the fluid measurement unit of FIG. 2.

FIG. 3 illustrates an example apparatus 300 that may be used to implement a portion of the formation sampling tool 200 associated with the pump 208, the fluid measurement unit 210, the pressure control unit 212, the flowline 214, the sensors 216, the reference database 228 and/or the analyzer 230 of FIG. 2. The example apparatus 300 includes a flowline 302 that includes a first flowline section 304, a second flowline section 306 and a third flowline section 308. A first valve 310 is positioned between the first and second flowline sections 304 and 306 and a second valve 312 is positioned between the second and third flowline sections 306 and 308. The first and second valves 310 and 312 are to control fluid flow through the flowline 302. Specifically, the first valve 310 may open to enable fluid to flow into the second flowline section 306 and the second valve 312 may close to prevent fluid from flowing out of the second flowline section 306. To retain a sample in the second flowline section 306, the first and second valves 310 and 312 may be closed. The valves 310 and 312 may be any suitable valve that may be operable in subterranean formation conditions.

To increase the pressure of the fluid sample in the second flowline section 306 to a predetermined pressure, the example apparatus 300 is provided with a pressure control unit 314. Specifically, in some examples, such as when the sample is a highly compressive gas at a relatively low pressure, increasing the pressure and, thus, increasing the density of the sample, advantageously enables more accurate measurements of the density to be obtained and/or concentration of at least the hydrocarbon constituents and the carbon dioxide in the sample.

To measure a characteristic of the sample in the second flowline section 306 once the pressure of the sample has been increased to the predetermined pressure, the example apparatus 300 is provided with a fluid measurement unit 316. Specifically, the fluid measurement unit 316 determines the fluid composition of the sample. Additionally, the fluid measurement unit 316 measures the partial densities of hydrocarbon constituents and carbon dioxide, which are substantially optically detectable, in the sample. However, the fluid measurement unit 316 may be advantageously utilized to measure any other characteristic(s) of the sample including, for example, any other substantially optically detectable component in the sample. The fluid measurement unit 316 is provided with a window 318 (e.g., an optical window) that is substantially adjacent a surface 320 of the second flowline section 306. The window 318 may be implemented using any suitable material such as a scratch resistant material (e.g., a sapphire material). The window 318 may be substantially flush with the surface 320 or the window 318 may be partially positioned within (e.g., extend into) the second flowline section 306.

To measure the temperature and the pressure of the sample, the example apparatus 300 is provided with a pressure sensor 322 and a temperature sensor 324. The measured values obtained using the fluid measurement unit 316 along with the temperature and pressure measurements may be advantageously utilized to determine a theoretical density of the sample in the second flowline section 306 based on a comparison by a processing unit 326 of the measured values with known reference values stored in, for example, a reference database 328. The known reference values may be reference values that were obtained from the subterranean formation being sampled or similar subterranean formations. Alternatively, the known reference values may be generated from laboratory experiments under controlled conditions.

In operation, to increase production of certain reservoirs such as, for example, the Cantarell field in Mexico, nonhydrocarbon fluids such as nitrogen may be injected into the formation (e.g., the formation F of FIG. 1) or into an adjacent wellbore (not shown). In some instances, the nitrogen may bypass the formation fluid and/or not obtain an equilibrium state in the formation fluid, thereby reducing the benefits gained by injecting the nitrogen into the formation. To determine or estimate the concentration of injected nitrogen in a formation fluid sample using the example apparatus 300, a pump 330, which may be used to implement the pump 208 of FIG. 2, pumps fluid (e.g., formation fluid) through the flowline 302 in a direction generally indicated by arrows 332. As the fluid moves through the flowline 302, the first and second valves 310 and 312 may actuate to a closed position to retain a sample within the second flowline section 306. In some examples, the second valve 312 may be actuated to the closed position before the first valve 310 is actuated to the closed position to ensure that a predetermined amount of fluid has entered the second flowline section 306.

The pressure control unit 314 then increases the pressure to a predetermined pressure. In some examples, the predetermined pressure is a pressure used during controlled laboratory experiments to generate known values (e.g., fluid characteristics) stored in the reference database 328. However, in other examples, the predetermined pressure may be a pressure at which relatively accurate measurements have been obtained by the fluid measurement unit 316. The pressure sensor 322 then measures the pressure of the sample and the processing unit 326 compares the measured pressure to the predetermined pressure to determine if the measured pressure is the same as or within an acceptable deviation from the predetermined pressure. If the pressure is not within an acceptable deviation from the predetermined pressure, the pressure control unit 314 again changes (e.g., increases or decreases) the pressure of the sample in the second flowline section 306 toward the predetermined pressure. However, in other examples, the measurements obtained via the fluid measurement unit 316 may be relatively accurate without having to control the pressure of the sample in the second flowline section 306 and, thus, the example apparatus 300 is not provided with the pressure control unit 314.

Figure 4:
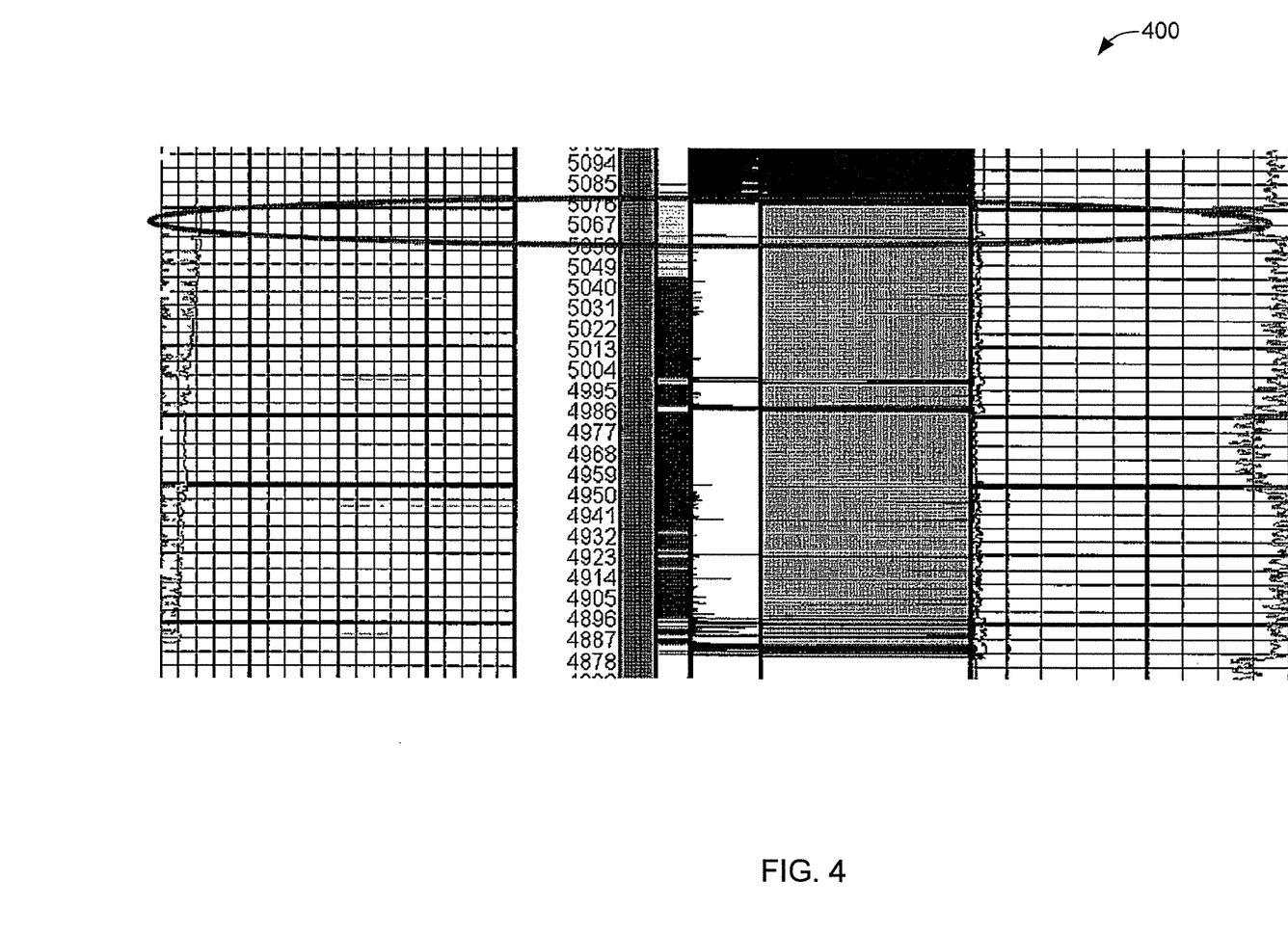
FIG. 4 depicts an example composition fluid analyzer log.

Once the measured pressure is the same as or within an acceptable deviation from the predetermined pressure, the fluid measurement unit 316 measures a first fluid composition (e.g., 100 wt % C1) of at least the hydrocarbon constituents and the carbon dioxide in the sample. Additionally, the fluid measurement unit 316 measures a first density (e.g., 0.110 g/cc) of at least the hydrocarbon constituents and the carbon dioxide in the sample. In some examples, the measured first density is used to determine and/or derive the weight percent of the component(s) in the sample. Turning briefly to FIG. 4, a composition fluid analyzer (CFA) log 400 indicates that, for example, the fluid measurement unit 316 has determined that the composition of the fluid sample is 100 wt % C1 at a density of 0.110 g/cc. The pressure sensor 322 and the temperature sensor 324 are then used to measure the pressure (e.g., 3700 psi) and the temperature (e.g., 64° C.) of the sample, respectively. These measured characteristics and/or parameters of the sample (e.g., the fluid composition of at least the hydrocarbon and the carbon dioxide, the pressure and the temperature) are then compared to known characteristics and/or parameters stored in the reference database 328 to determine a first theoretical density (e.g., 0.157 g/cc) of the fluid.

An analyzer 334 then compares and determines a first difference (e.g., 0.047 g/cc) (e.g., a portion) between the first theoretical density (e.g., 0.157 g/cc) and the first measured density (e.g., 0.0110 g/cc). In some examples, the analyzer 334 may be implemented with a NIST 14 program to determine an equation of state. However, in other examples, any other suitable program may be used to determine the equation of state. Additionally, the analyzer 334 determines if the first difference is at or below a predetermined parameter or threshold. As discussed above, the first difference is associated with a concentration and/or density of nitrogen in the fluid sample. In particular, because the theoretical density is based on composition information obtained by the fluid measurement unit 316, which measures the composition of optically detectable fluids, any amount by which the theoretical density exceeds the measured density, which includes measured concentrations of partial densities of the substantially optically detectable fluids, can be attributed to substantially non-optically detectable components such as nitrogen, hydrogen sulfide and/or helium.

In operation, the fluid measurement unit 316 measures the first density of the hydrocarbon and the carbon dioxide in the sample and, thus, any nitrogen in the sample is not measured and/or accounted for. Additionally, a first theoretical density is determined based on a fluid composition that comprises hydrocarbon and carbon dioxide at the measured temperature and pressure, which also does not account for nitrogen in the sample. Thus, a difference may exist between the first theoretical density and the first measured density of the hydrocarbon and the carbon dioxide because a fluid comprising the measured composition of hydrocarbon and carbon dioxide would not theoretically exist at the measured pressure and temperature. However, if the sample instead comprised only hydrocarbon and carbon dioxide (e.g., substantially optically detectable fluids), there may be no substantial difference between the first theoretical density and the first measured density, which would indicate that there is no density contribution in the sample from substantially non-optically detectable fluids such as nitrogen.

If the analyzer 334 determines that the first difference is not at or below the predetermined parameter, the processing unit 326 determines a second fluid composition (e.g., 70 wt % C1 and 30 wt % $N_2$) based on the first fluid composition and the first difference. Specifically, the second fluid composition includes both the first fluid composition of the hydrocarbon and the carbon dioxide as well as the determined concentration of nitrogen in the sample. The processing unit 326 then determines a second density (e.g., 0.157 g/cc) of the sample. Specifically, the second density of the sample is equal to the previously determined first theoretical density (e.g., 0.157 g/cc), which includes the first density (e.g., 0.110 g/cc) of the hydrocarbon and the carbon dioxide in the sample and the determined density (e.g., 0.047 g/cc) of the nitrogen in the sample. As discussed above, the first difference may be used to determine and/or derive the weight percent of nitrogen in the sample.

The processing unit 326 then determines a second theoretical density (e.g., 0.171 g/cc) based on the second fluid composition (e.g., 70 wt % C1 and 30 wt % $N_2$) at the measured pressure (e.g., 3700 psi) and temperature (e.g., 64° C.). The analyzer 334 then compares and determines a second difference (e.g., 0.014 g/cc) (e.g., another portion) between the second density (e.g., 0.157 g/cc) and the second theoretical density (e.g., 0.171 g/cc). The second difference is also associated with the concentration of nitrogen in the sample. Additionally, the analyzer 334 determines if the difference is at or below the predetermined parameter or threshold.

If the analyzer 334 determines that the second difference is not at or below the predetermined parameter, the processing unit 326 determines a third fluid composition (e.g., 64 wt % C1 and 36 wt % $N_2$) based on the second fluid composition and the second difference. Additionally, the processing unit 326 determines a third density (e.g., 0.171 g/cc) that is equal to the second theoretical density. Then the processing unit 326 determines a third theoretical density (e.g., 0.174 g/cc) based on the third fluid composition and the measured pressure and temperature, which is then compared by the analyzer 334 to the third density to determine a third difference (e.g., 0.003 g/cc).

Generally, as described above, the processing unit 326 and the analyzer 334 can iteratively determine the fluid composition of a fluid sample based on the difference associated with the nitrogen concentration in the sample and iteratively determine the theoretical density based on the determined fluid composition, which may include the portion associated with nitrogen, the measured pressure and temperature until the difference is at or below a predetermined parameter or threshold (e.g., 0.01 g/cc) or until a predetermined number of iterations have taken place (e.g., ten iterations).

If the difference is at or below the predetermined parameter or threshold or if the predetermined number of iterations have taken place, the first and second valves 310 and 312 may actuate to an open position and the sample may flow through the second valve 312 in the direction generally represented by the arrows 332. Once the sample flows out of the second flowline section 306, the first and second valves 310 and 312 may actuate to the closed position and the above-described process may be repeated.

Figure 5:
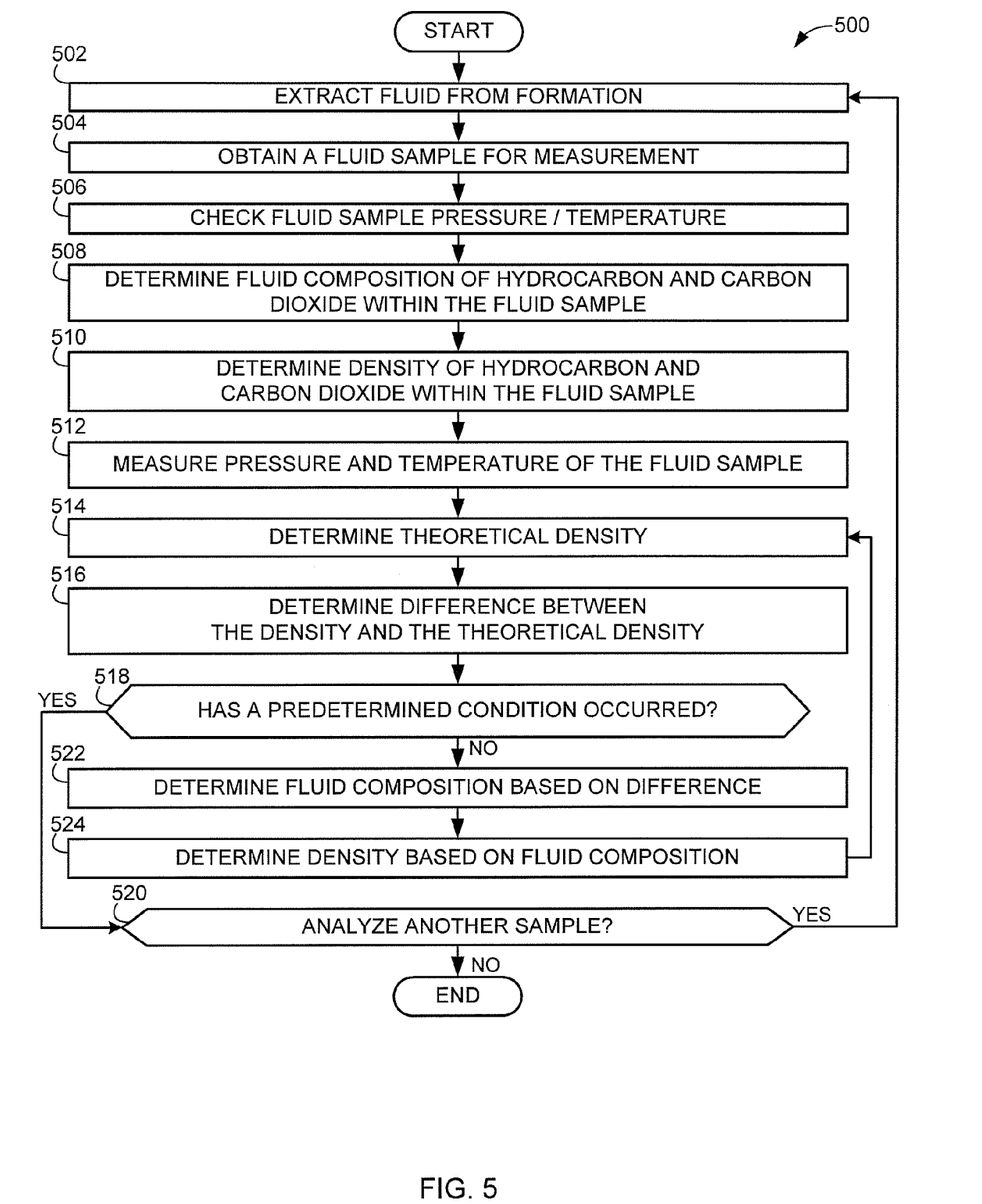
FIG. 5 is a flow diagram of an example method that may be used with the example apparatus described herein to identify fluid components in formation fluid samples.

FIG. 5 is a flowchart of an example method 500 that can be used in conjunction with the example apparatus described herein to draw and analyze formation fluid samples from a subterranean formation (e.g., the formation F of FIG. 1). The example method of FIG. 5 may be used to implement the example formation tester 114 of FIG. 1, the formation sampling tool 200 of FIG. 2, and the example apparatus 300 of FIG. 3. The example method of FIG. 5 may be implemented using software and/or hardware. In some example implementations, the flowchart can be representative of example machine readable instructions, and the example method of the flowchart may be implemented entirely or in part by executing the machine readable instructions. Such machine readable instructions may be executed by the electronics and processing system 106 (FIG. 1) and/or the processing units 226 (FIG. 2) or 326 (FIG. 3). In particular, a processor or any other suitable device to execute machine readable instructions may retrieve such instructions from a memory device (e.g., a random access memory (RAM), a read only memory (ROM), etc.) and execute those instructions. In some example implementations, one or more of the operations depicted in the flowchart of FIG. 5 may be implemented manually. Although the example method is described with reference to the flowchart of FIG. 5, persons of ordinary skill in the art will readily appreciate that other methods to implement the example formation tester 114 of FIG. 1, the formation sampling tool 200 of FIG. 2, and the example apparatus 300 of FIG. 3 to analyze formation fluid samples may additionally or alternatively be used. For example, the order of execution of the blocks depicted in the flowchart of FIG. 5 may be changed and/or some of the blocks described may be rearranged, eliminated, or combined.

The example method 500 may be used to draw and analyze formation fluid using, for example, the formation sampling tool 200 of FIG. 2. Initially, the probe assembly 202 (FIG. 2) extracts (e.g., admits, draws, etc.) fluid from the formation F (block 502) and the valve 232 (FIG. 2) or the valves 310 and 312 of FIG. 3 actuate to an open position enabling a sample of the fluid to flow into the flowline 214 (FIG. 2) or the second flowline section 306 (FIG. 3). Once a predetermined amount of fluid has entered the flowline 214 (FIG. 2) or the second flowline section 306 (FIG. 3), the valve 232 (FIG. 2) or the valves 310 and 312 (FIG. 3) are actuated to the closed position to obtain a fluid sample for measurement (block 504).

The fluid measurement unit 210 (FIG. 2) or 316 (FIG. 3) and/or the sensors 216 (FIG. 2), the pressure sensor 322 (FIG. 3) and/or the temperature sensor 324 (FIG. 3) then analyze or check the fluid sample (block 506). In some examples, as discussed above, the pressure sensor 322 (FIG. 3) measures the pressure of the sample and the processing unit 226 (FIG. 2) or 326 (FIG. 3) compares the measured pressure to a predetermined pressure. If the pressure is not within an acceptable deviation from the predetermined pressure, the pressure control unit 212 (FIG. 2) or 314 (FIG. 3) changes (e.g., increases) the pressure of the sample within the flowline 214 (FIG. 2) or the second flowline section 306 toward the predetermined pressure to increase the accuracy of the measurements obtained. However, in other examples, the example formation sampling tool 200 (FIG. 2) and/or the example apparatus 300 (FIG. 3) may not be provided with the pressure control unit 212 (FIG. 2) or 314 (FIG. 3).

The fluid measurement unit 210 (FIG. 2) or 316 (FIG. 3) then determines the fluid composition of the hydrocarbon and the carbon dioxide in the fluid sample (block 508). Additionally, the fluid measurement unit 210 (FIG. 2) or 316 (FIG. 3) determines the density of the hydrocarbon and the carbon dioxide in the fluid sample (block 510). The pressure sensor 322 (FIG. 3) and the temperature sensor 324 (FIG. 3) or at least some of the sensors 216 (FIG. 2) then measure the pressure and the temperature of the sample, respectively (block 512).

The fluid composition of the hydrocarbon and the carbon dioxide and the measured pressure and temperature are then compared to known characteristics and/or parameters stored in the reference database 107 (FIG. 1), 228 (FIG. 2) and/or 328 (FIG. 3) to determine a theoretical density of the fluid sample based on the measured composition, pressure and temperature (block 514).

The analyzer 230 (FIG. 2) or 334 (FIG. 3) then determines a difference between the density and the theoretical density (block 516). As discussed above, the difference is associated with the concentration of nitrogen in the sample. Additionally, the analyzer 230 (FIG. 2) or 334 (FIG. 3) then determines if a predetermined condition has occurred (block 518). Specifically, the analyzer 230 (FIG. 2) or 334 (FIG. 3) determines if the difference is at or below a predetermined amount or threshold (e.g., 0.01 g/cc) and/or if a predetermined number of iterations have occurred. If the analyzer 230 (FIG. 2) or 334 (FIG. 3) determines that the predetermined condition has occurred, the processing unit 226 (FIG. 2) or 326 (FIG. 3) then determines whether it should analyze another formation fluid sample (block 520). For example, if the formation sampling tool 200 (FIG. 2) has drawn another formation fluid sample and the processing unit 226 (FIG. 2) or 326 (FIG. 3) has not received an instruction or command to stop analyzing fluid, the processing unit 226 (FIG. 2) or 326 (FIG. 3) may determine that it should analyze another fluid sample (block 520). Otherwise, the example process of FIG. 5 is ended.

However, if the analyzer 230 (FIG. 2) or 334 (FIG. 3) determines that the predetermined condition has not occurred, the processing unit 226 (FIG. 2) or 326 (FIG. 3) re-determines the fluid composition based on the difference (block 522) between the density and the theoretical density. Specifically, the fluid composition includes the fluid composition of the hydrocarbon and the carbon dioxide in the sample along with the difference(s), which is associated with the amount of nitrogen in the sample. The processing unit 226 (FIG. 2) or 326 (FIG. 3) then re-determines the density of the fluid sample, which is equal to the previously determined theoretical density, based on the difference (block 524). Specifically, the density includes the density of the hydrocarbon and the carbon dioxide in the sample along with the difference (s), which is associated with the concentration of nitrogen in the sample. Control then returns to block 514 where the theoretical density is re-determined based on the fluid composition determined in block 522. The example process of blocks 514, 516, 518, 522 and 524 iteratively repeat until the predetermined condition has occurred (block 518).

If the analyzer 230 (FIG. 2) or 334 (FIG. 3) determines that the predetermined condition has occurred, the processing unit 226 (FIG. 2) or 326 (FIG. 3) then determines whether it should analyze another formation fluid sample (block 520). For example, if the formation sampling tool 200 (FIG. 2) has drawn another formation fluid sample and the processing unit 226 (FIG. 2) or 326 (FIG. 3) has not received an instruction or command to stop analyzing fluid, the processing unit 226 (FIG. 2) or 326 (FIG. 3) may determine that it should analyze another fluid sample (block 520). Otherwise, the example process of FIG. 5 is ended.

Figure 6:
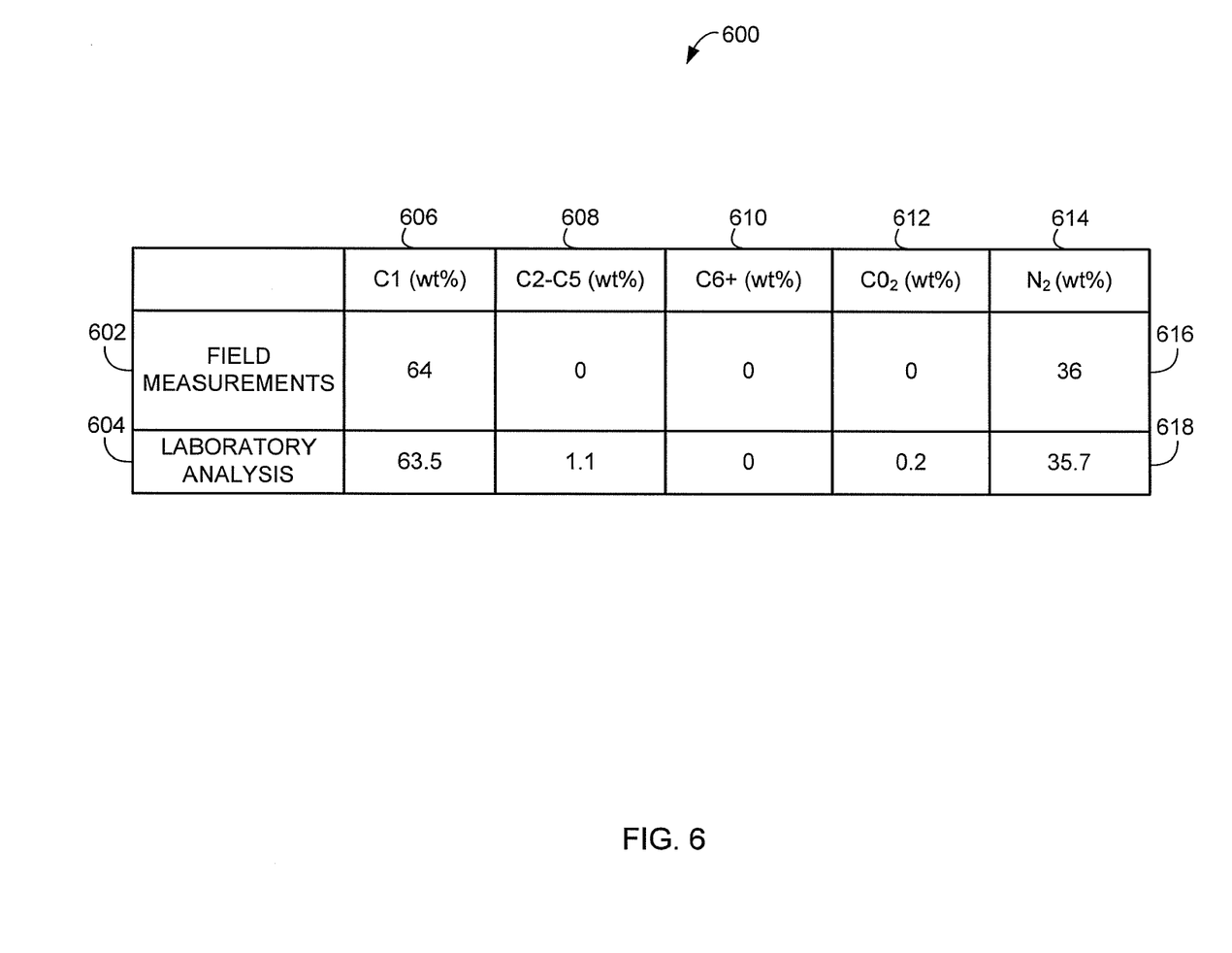
FIG. 6 is a table that depicts results obtained using the methods and apparatus described herein.

FIG. 6 depicts a table 600 that shows test results of field measurements 602 obtained using the examples described herein and results obtained using known laboratory analysis techniques 604. Specifically, a sample was measured downhole by, for example, the example formation tester 114 of FIG. 1, the formation sampling tool 200 of FIG. 2, and/or the example apparatus 300 of FIG. 3 and thereafter a the sample was brought to the surface where measurements were obtained using known laboratory analysis techniques. In some instances, relatively more accurate measurements may be obtained using known laboratory analysis techniques because constraints such as, for example, available space and/or available power, which are encountered in the downhole environment, are not applicable in the laboratory.

As shown in the table 600, the weight percent (e.g., mass percent) of C1 (606), C2-C5 (608), C6+ (610), carbon dioxide ($CO_2$) (612) and nitrogen ($N_2$) (614) in the sample were measured downhole and in the laboratory. A comparison between the results of the field measurements 602 and the laboratory analysis 604 indicate that there is an inconsequential difference between the two sets of results. Specifically, the measurements obtained using the example methods and apparatus described herein determined the weight percent of nitrogen (614) in the sample to be 36 wt % (616) while the laboratory analysis 604 determined the weight percent of nitrogen (614) in the sample to be 35.7 wt % (618). As shown, the results obtained using the example methods and apparatus described herein can be advantageously utilized to accurately determine the concentration of nitrogen within the downhole fluid to, for example, determine if the injected nitrogen bypassed the formation fluid and/or to determine if the injected nitrogen did not obtain an equilibrium state in the formation fluid FIG. 7 is a schematic diagram of an example processor platform P100 that may be used and/or programmed to implement to implement the electronics and processing system 106, the processing units 226 and 326, the fluid measurement units 210 and 316, and the analyzers 230 and 334. For example, the processor platform P100 can be implemented by one or more general purpose processors, processor cores, microcontrollers, etc.

The processor platform P100 of the example of FIG. 7 includes at least one general purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example methods and apparatus described herein.

The processor P105 is in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown).

The processor platform P100 also includes an interface circuit P130. The interface circuit P130 may be implemented by any type of interface standard, such as an external memory interface, serial port, general purpose input/output, etc. One or more input devices P135 and one or more output devices P140 are connected to the interface circuit P130.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. An apparatus to determine a concentration of nitrogen in a downhole fluid, comprising:
    a fluid measurement unit to measure a first fluid composition and a density of at least a hydrocarbon and carbon dioxide in a sample of the downhole fluid;
    one or more sensors to measure at least a pressure and a temperature of the sample;
    a processing unit to determine a first theoretical density based on at least the first fluid composition, the temperature, and the pressure of the sample; and
    an analyzer to determine a first difference between the density of at least the hydrocarbon and the carbon dioxide in the sample and the first theoretical density, wherein the first difference is associated with a concentration of nitrogen in the sample.

2. The apparatus as defined in claim 1, wherein the processing unit is to determine a second theoretical density based on at least the temperature and the pressure of the sample and a second fluid composition based on the first fluid composition and the first difference.

3. The apparatus as defined in claim 2, wherein the analyzer is to determine a second difference between the second theoretical density and the first theoretical density, and wherein the second difference is associated with the concentration of nitrogen in the sample.

4. The apparatus as defined in claim 1, wherein the concentration of nitrogen is substantially zero when the first difference is substantially zero.

5. The apparatus as defined in claim 1, wherein the fluid measurement unit is a spectrometer.

6. The apparatus as defined in claim 1, further comprising a pressure control unit to change the pressure of the sample to increase an accuracy of measurement of the density of at least the hydrocarbon and the carbon dioxide in the sample.

7. A method of determining a concentration of nitrogen in a downhole fluid, comprising:
    obtaining a sample of a downhole fluid;
    analyzing the sample to determine a first fluid composition and a density of at least a hydrocarbon and carbon dioxide in the sample;
    measuring a pressure and a temperature of the sample;
    determining a first theoretical density based on at least the first fluid composition, the temperature, and the pressure of the sample; and
    determining a first difference between the density of at least the hydrocarbon and the carbon dioxide in the sample and the first theoretical density, wherein the first difference is associated with a concentration of nitrogen in the sample.

8. The method as defined in claim 7, further comprising determining a second theoretical density based on at least the temperature and the pressure of the sample and a second fluid composition based on the first fluid composition and the first difference associated with the concentration of nitrogen in the sample.

9. The method as defined in claim 8, further comprising determining a second difference between the second theoretical density and the first theoretical density, wherein the second difference is associated with the concentration of nitrogen in the sample.

10. The method as defined in claim 7, further comprising increasing the pressure of the sample to increase an accuracy of the determined density of at least the hydrocarbon and the carbon dioxide in the sample.

11. An apparatus to determine a concentration of substantially non-optically detectable fluid in a downhole fluid, comprising:
    a fluid measurement unit to measure a first fluid composition and a density of a substantially optically detectable fluid in a sample of the downhole fluid;
    one or more sensors to measure at least a pressure and a temperature of the sample;
    a processing unit to determine a first theoretical density based on at least the first fluid composition, the temperature, and the pressure of the sample; and
    an analyzer to determine a first difference between the density of the substantially optically detectable fluid and the first theoretical density, wherein the first difference is associated with a concentration of the substantially non-optically detectable fluid in the sample.

12. The apparatus as defined in claim 11, wherein the substantially non-optically detectable fluid is at least one of injected nitrogen, naturally occurring nitrogen, naturally occurring hydrogen sulfide, or naturally occurring helium.

13. The apparatus as defined in claim 11, wherein the substantially optically detectable fluid comprises at least a hydrocarbon and carbon dioxide.

14. The apparatus as defined in claim 11, wherein the processing unit is to determine a second theoretical density based on at least the temperature and the pressure of the sample and a second fluid composition that includes the first fluid composition and the first difference associated with the concentration of the substantially non-optically detectable fluid.

15. An apparatus to determine a concentration of nitrogen in a downhole fluid, comprising:
- means to measure a first fluid composition and a density of at least a hydrocarbon and carbon dioxide in a fluid sample;
- means to measure at least a pressure and a temperature of the fluid sample;
- means for determining a first theoretical density based on the first fluid composition, the pressure, and the temperature; and
- means for determining a portion of the fluid sample associated with a concentration of nitrogen based on the first theoretical density.

16. The apparatus as defined in claim 15, wherein the means for determining the first theoretical density comprises a processing unit to determine the first theoretical density based on at least the first fluid composition, the temperature, and the pressure of the fluid sample.

17. The apparatus as defined in claim 16, wherein the means for determining the portion of the fluid sample associated with the concentration of nitrogen comprises an analyzer to determine a first difference between the density of at least the hydrocarbon and the carbon dioxide in the sample and the first theoretical density, wherein the first difference is the portion.

18. The apparatus as defined in claim 15, further comprising means for determining a second theoretical density.

19. The apparatus as defined in claim 18, wherein the means for determining the second theoretical density comprises a processing unit that determines the second theoretical density based on at least the temperature and the pressure of the fluid sample and a second fluid composition that includes the first fluid composition and the portion of the sample associated with the concentration of nitrogen.

20. The apparatus as defined in claim 19, further comprising means for determining another portion of the sample associated with the concentration of nitrogen.

21. The apparatus as defined in claim 20, wherein the means for determining the other portion of the sample associated with the concentration of nitrogen comprises an analyzer to determine a second difference between the second theoretical density and the first theoretical density, wherein the second difference is the other portion.

22. A method of determining a concentration of nitrogen in a downhole fluid, comprising:
(a) obtaining a sample of a downhole fluid;
(b) analyzing the sample to determine a fluid composition and a density of at least a hydrocarbon and carbon dioxide in the sample;
(c) measuring a pressure and a temperature of the sample;
(d) determining a theoretical density based on at least the fluid composition, the temperature, and the pressure of the sample;
(e) determining a difference between the density and the theoretical density, wherein the difference is associated with a concentration of nitrogen in the sample;
(f) re-determining the fluid composition based on the difference;
(g) re-determining the density based on the difference; and
(h) repeating (d)-(g) at least a predetermined number of times or until the difference is at or below a predetermined threshold.

* * * * *